(12) United States Patent
Dickie et al.

(10) Patent No.: US 9,131,765 B2
(45) Date of Patent: Sep. 15, 2015

(54) BRUSH HEAD FOR AN ELECTRIC TOOTHBRUSH

(71) Applicant: Brushpoint Innovations Inc, King City (CA)

(72) Inventors: Robert G. Dickie, King City (CA); Shahram Nabavi, King City (CA)

(73) Assignee: Brushpoint Innovations Inc, King City, Ontario (CA)

( * ) Notice: Subject to any disclaimer, the term of this patent is extended or adjusted under 35 U.S.C. 154(b) by 60 days.

(21) Appl. No.: 13/769,667

(22) Filed: Feb. 18, 2013

(65) Prior Publication Data
US 2014/0173838 A1    Jun. 26, 2014

Related U.S. Application Data

(60) Provisional application No. 61/739,937, filed on Dec. 20, 2012.

(51) Int. Cl.
*A46B 9/04* (2006.01)
*A61C 17/22* (2006.01)

(52) U.S. Cl.
CPC ............... *A46B 9/04* (2013.01); *A61C 17/222* (2013.01)

(58) Field of Classification Search
CPC ........... A46B 7/08; A46B 9/04; A61C 17/222
USPC ........................ 15/22.1, 28, 105, 167.1, 180
See application file for complete search history.

(56) References Cited

U.S. PATENT DOCUMENTS

| | | | |
|---|---|---|---|
| 2,080,605 A | 5/1937 | Duey | |
| 2,140,307 A | 12/1938 | Belaschk et al. | |
| 2,155,245 A | 4/1939 | Sekine | |
| 2,558,332 A | 6/1951 | Artale | |
| 2,879,532 A * | 3/1959 | Szabo et al. | 401/24 |
| D266,116 S | 9/1982 | Deconinck | |
| 4,399,582 A | 8/1983 | Ernest et al. | |
| D295,342 S | 4/1988 | van Asten | |
| D305,480 S | 1/1990 | Yuen | |
| D307,216 S | 4/1990 | Yuen | |
| D326,778 S | 6/1992 | Vetter | |
| 5,142,724 A | 9/1992 | Park | |
| 5,289,604 A | 3/1994 | Kressner | |
| 5,416,942 A | 5/1995 | Baldacci et al. | |
| 5,467,495 A | 11/1995 | Boland et al. | |
| 5,499,420 A | 3/1996 | Boland | |
| 5,577,285 A | 11/1996 | Drossler | |

(Continued)

FOREIGN PATENT DOCUMENTS

CA       2742911        5/2010
WO    WO 0160281 A1 *  8/2001

*Primary Examiner* — Monica Carter
*Assistant Examiner* — Michael Jennings
(74) *Attorney, Agent, or Firm* — Sand & Sebolt

(57) ABSTRACT

A brush head for an electric toothbrush having a support structure rotatably oscillated by a motor in the handle of the toothbrush. A plurality of bristle tufts are mounted on the support structure in three ring-like series concentrically about a center point of the support structure. The bristle tufts are arranged in a unique arrangement whereby no more than two of the bristle tufts in the intermediate series and innermost series lie on a diameter line passing through the center point. The outermost and intermediate series of bristle tufts may be arranged in oval-shaped rings and the bristle tufts of the inner series may have a circular arrangement. All of the tufts preferably have the same height and diameter.

16 Claims, 5 Drawing Sheets

(56) References Cited

U.S. PATENT DOCUMENTS

| | | | |
|---|---|---|---|
| 5,625,916 A | 5/1997 | McDougall | |
| 5,652,990 A | 8/1997 | Driesen et al. | |
| 5,732,433 A | 3/1998 | Gocking et al. | |
| 5,867,856 A | 2/1999 | Herzog | |
| 5,926,897 A | 7/1999 | Volpenhein | |
| 6,018,840 A | 2/2000 | Guay et al. | |
| 6,021,538 A * | 2/2000 | Kressner et al. | 15/28 |
| 6,035,476 A | 3/2000 | Underwood et al. | |
| 6,058,541 A | 5/2000 | Masterman et al. | |
| 6,178,583 B1 | 1/2001 | Volpenhein | |
| 6,195,828 B1 | 3/2001 | Fritsch | |
| 6,308,359 B2 | 10/2001 | Fritsch et al. | |
| 6,360,395 B2 | 3/2002 | Blaustein et al. | |
| 6,363,565 B1 | 4/2002 | Paffrath | |
| 6,367,108 B1 | 4/2002 | Fritsch et al. | |
| 6,574,820 B1 | 6/2003 | DePuydt et al. | |
| 6,588,042 B2 | 7/2003 | Fritsch et al. | |
| 6,665,901 B2 * | 12/2003 | Driesen et al. | 15/167.1 |
| 6,892,413 B2 * | 5/2005 | Blaustein et al. | 15/22.2 |
| 6,966,093 B2 * | 11/2005 | Eliav et al. | 15/22.1 |
| 7,322,066 B2 | 1/2008 | Ping et al. | |
| D577,199 S | 9/2008 | Zhuan | |
| 7,614,107 B2 * | 11/2009 | Cobabe et al. | 15/28 |
| 7,690,067 B2 | 4/2010 | Schaefer et al. | |
| 7,698,771 B2 | 4/2010 | Gall | |
| 7,788,756 B2 * | 9/2010 | Kraemer | 15/28 |
| 7,934,284 B2 | 5/2011 | Braun et al. | |
| 7,941,886 B2 | 5/2011 | Chenvainu et al. | |
| 7,958,589 B2 | 6/2011 | Braun et al. | |
| 8,166,601 B2 * | 5/2012 | Brown et al. | 15/201 |
| 8,250,694 B2 * | 8/2012 | Gatzemeyer et al. | 15/22.1 |
| 8,302,238 B2 * | 11/2012 | Biro et al. | 15/22.1 |
| 8,444,416 B2 * | 5/2013 | Chenvainu et al. | 433/80 |
| 8,621,699 B2 * | 1/2014 | Fischer et al. | 15/28 |
| 2002/0108194 A1 * | 8/2002 | Carlucci et al. | 15/28 |
| 2003/0084525 A1 * | 5/2003 | Blaustein et al. | 15/22.1 |
| 2003/0084528 A1 * | 5/2003 | Chan et al. | 15/22.1 |
| 2003/0106175 A1 * | 6/2003 | Lam | 15/28 |
| 2004/0060134 A1 * | 4/2004 | Eliav et al. | 15/22.1 |
| 2005/0132513 A1 * | 6/2005 | Eliav et al. | 15/22.1 |
| 2005/0278877 A1 * | 12/2005 | Akridge et al. | 15/28 |
| 2007/0199168 A1 * | 8/2007 | Blanchard et al. | 15/105 |
| 2009/0025157 A1 * | 1/2009 | Gatzemeyer et al. | 15/28 |
| 2010/0162499 A1 | 7/2010 | Braun et al. | |
| 2010/0162500 A1 | 7/2010 | Hilscher et al. | |
| 2010/0306941 A1 * | 12/2010 | Erskine-Smith et al. | 15/167.1 |
| 2011/0016647 A1 * | 1/2011 | Biro et al. | 15/22.1 |
| 2011/0138560 A1 * | 6/2011 | Vitt et al. | 15/167.1 |
| 2011/0283470 A1 * | 11/2011 | Gatzemeyer et al. | 15/28 |
| 2012/0204371 A1 * | 8/2012 | Chun et al. | 15/167.1 |
| 2013/0007969 A1 * | 1/2013 | Driesen et al. | 15/28 |
| 2013/0031733 A1 * | 2/2013 | Gatzemeyer et al. | 15/22.1 |
| 2013/0086759 A1 * | 4/2013 | Fischer et al. | 15/22.1 |

* cited by examiner

BRUSH HEAD FOR AN ELECTRIC TOOTHBRUSH

CROSS-REFERENCE TO RELATED APPLICATION

This application claims priority from U.S. Provisional Application Ser. No. 61/739,937, filed Dec. 20, 2012, the disclosure of which is incorporated herein by reference.

BACKGROUND OF THE INVENTION

1. Technical Field

The present invention relates to toothbrushes, and more particularly, to the brush head for an electric toothbrush. More particularly, the invention relates to a unique arrangement of tuft bristles which are mounted on and extend upwardly from a support structure of the brush head.

2. Background Information

Electric toothbrushes consist generally of a handle containing an electric motor and a battery supply for the motor for driving a brush head mounted at the end of a tube attached to the handle. The brush head is usually moved in a rotating oscillating type motion by a drive shaft extending from the motor through the connecting tube. This moves the bristle tufts alone or in combination with flexible elastomeric strips, to provide a cleaning action to a user's teeth and gums. A considerable number of bristle tuft and elastic strip arrangements have been used on prior art brush heads, all of which are intended to provide various types of cleaning action to the teeth. Some examples of prior art bristle tuft arrangements for brush heads for electric toothbrushes are shown in U.S. Pat. Nos. 5,416,942; 5,467,495; 5,625,916; 5,652,990; 6,021,538; 6,665,901; 7,698,771; 7,934,284; 7,941,886 and 7,958,589. All of these prior art brush head bristle tuft arrangements are intended to provide some type of desired cleaning action to the teeth, many of which provide the desired sought after effect. Some of these prior art bristle tufts arrangements attempt to achieve their intended result by the various configurations of the bristle tufts as well as the type of materials together with specific heights and diameters of the bristle tufts.

The present invention provides a unique bristle tuft arrangement which is simple and economical to manufacture and which is believed to provide a quality cleaning action when used in a rotary oscillating manner on the end of an electric driven toothbrush.

BRIEF SUMMARY OF THE INVENTION

One aspect of the present invention is to provide for a relatively simple but effective brush head for cleaning teeth adapted to be mounted on the end of an electric toothbrush. The brush head has three series of bristle tufts each of which is a ring-shaped series of bristle tufts arranged concentrically with respect to each other and about a center point of a brush head support surface on which the bristles are mounted and extend therefrom. The outer ring or series of bristle tufts preferably has a generally oval-shaped arrangement and comprises 16 equally circumferentially spaced bristle tufts. An intermediate ring or series of bristle tufts preferably has a generally oval-shaped arrangement and consists of six bristle tufts, wherein an inner series of bristle tufts forms a generally circular inner ring consisting of six bristle tufts equally circumferentially spaced with respect to each other as are the individual bristle tufts of the outer and intermediate ring-shaped series of bristle tufts. A single bristle tuft preferably is located at the center point of the support surface of the brush head. All of the bristle tufts of the three series and center bristle tuft preferably are of equal length and diameter greatly facilitating the manufacture and economy of the brush head.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE PREFERRED EMBODIMENT

Figure 1:
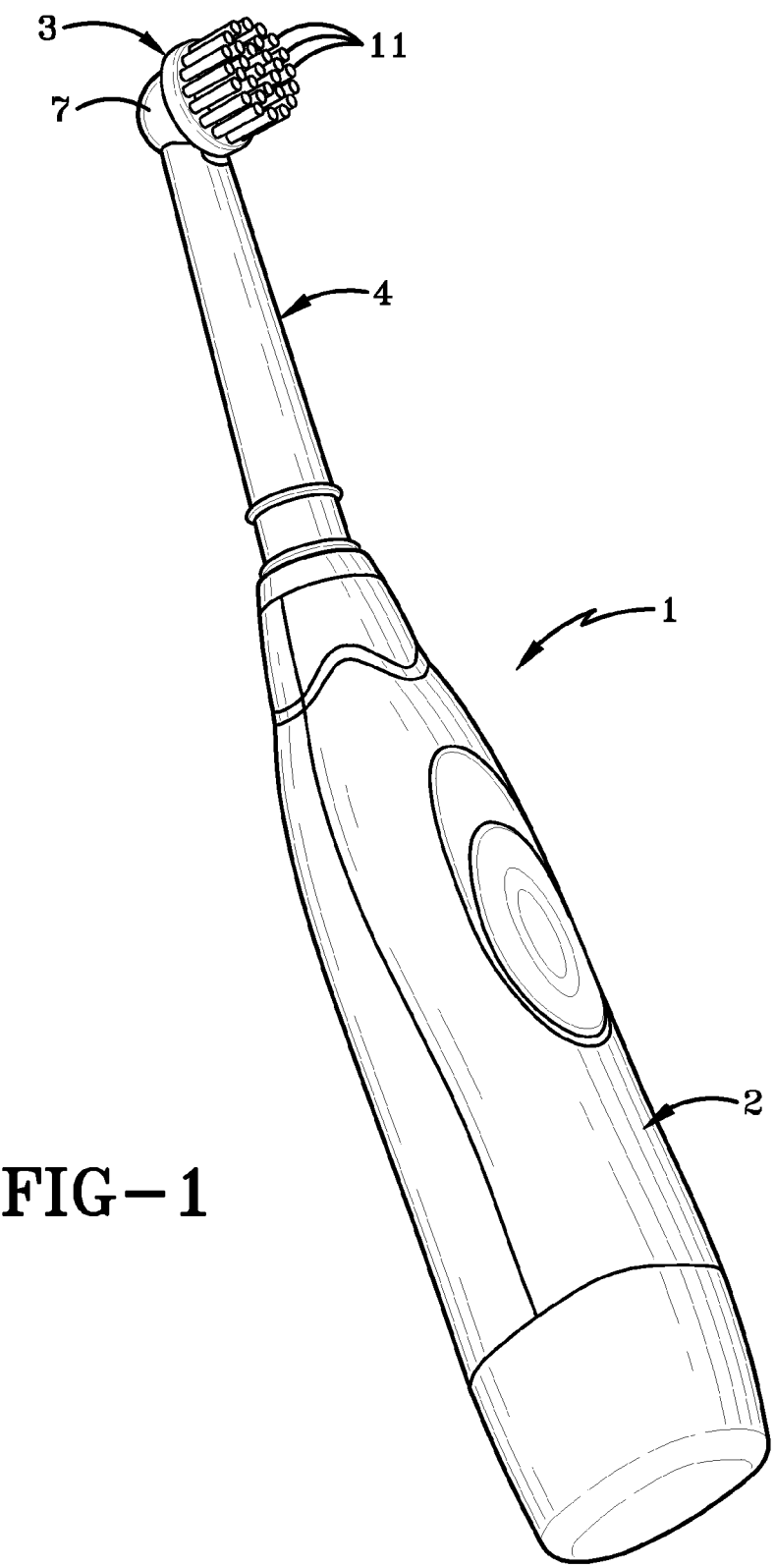
FIG. 1 is a perspective view of a usual type of electric toothbrush having the brush head of the present invention mounted thereon.

The toothbrush of the present invention is indicated generally at 1, and is shown in FIG. 1. Toothbrush 1 is of usual construction consisting of a handle 2 which contains an electric motor powered by a battery and which is connected to the brush head 3 by a tube 4 through which a driveshaft connects the internal motor with a gear mechanism for rotationally oscillating the brush head 3. The particular internal arrangement of the motor, battery and connecting driveshaft and gear mechanism can vary but is well known in the art. Some examples are shown in U.S. Pat. Nos. 5,467,495; 5,499,420; 6,195,828; 5,867,856; 5,577,285 and 5,289,604.

The particular configuration of the handle, drive motor, connecting shaft and support tube shown in FIG. 1 is merely one example of the type of electric toothbrush structure which can be utilized in supporting and rotating brush head 3 of the present invention. Preferably, brush head 3 will be rotated in an oscillating alternating rotary motion to provide the desired cleaning effect but could have other motion without effecting the invention.

Figure 2:
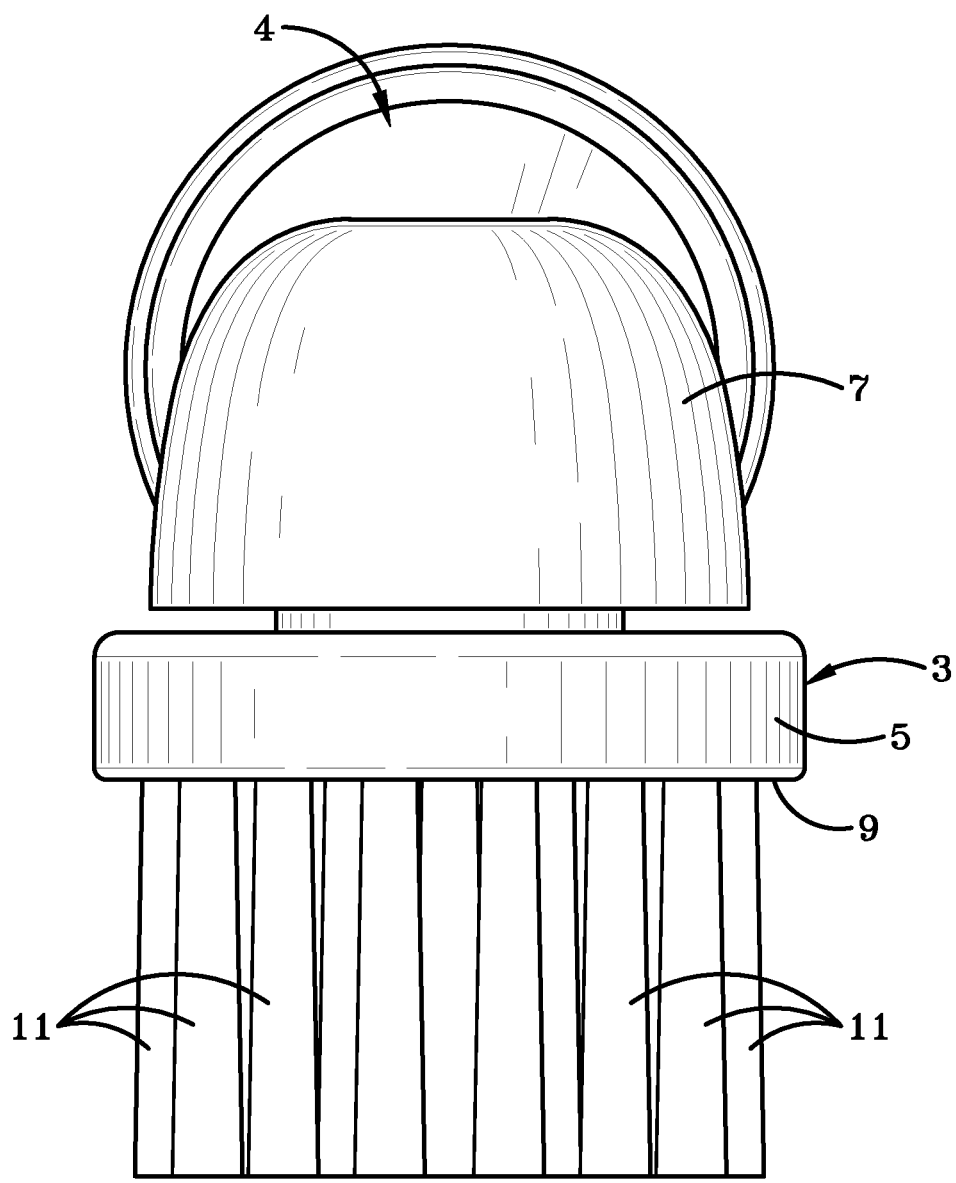
FIG. 2 is a greatly enlarged front elevational view of the brush head of the present invention.
Figure 3:
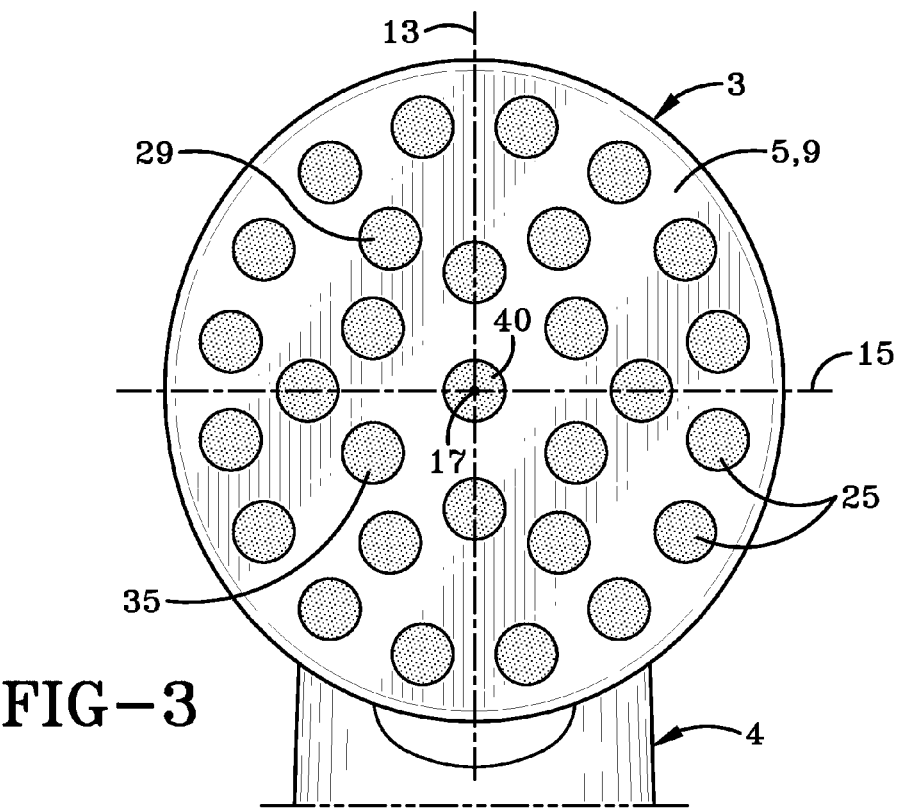
FIG. 3 is a plan view showing the generally oval-shaped support surface of the brush head of the present invention with the major and minor axes indicated thereon.

Brush head 3 is shown in further detail in FIG. 2 and includes a support member 5 which is connected to the extended end 7 of tube 4 and has an outer generally planar support surface 9 from which a plurality of bristle tufts indicated generally at 11 extend outwardly therefrom in a generally perpendicular relationship with respect to surface 9. In accordance with one of the features of the invention, each of the bristle tufts 11 is formed of a plurality of bristles which can be made of various types of filament materials and assembled and embedded in support member 5 in a manner well known in the toothbrush cleaning art. The bristles which form the tufts have the same length as shown in FIG. 2, and when assembled have the same tuft diameter best shown in FIGS. 4-7. This uniformity of the bristle tufts provides for a more economically produced brush head than varying the height, size and material of the bristle tufts as done in many prior art bristle tufts.

The unique arrangement of the bristle tufts is shown particularly in FIGS. 3-7. Support surface 9 (FIG. 3) preferably has a slightly oval-shaped configuration having a major axis 13 and a minor axis 15 which intersect at a center point 17. The unique bristle tuft arrangement consists of three series of bristle tufts with a first or outer series indicated generally at 19, an intermediate or second series 21, and an inner or third series indicated generally at 23.

Figure 4:
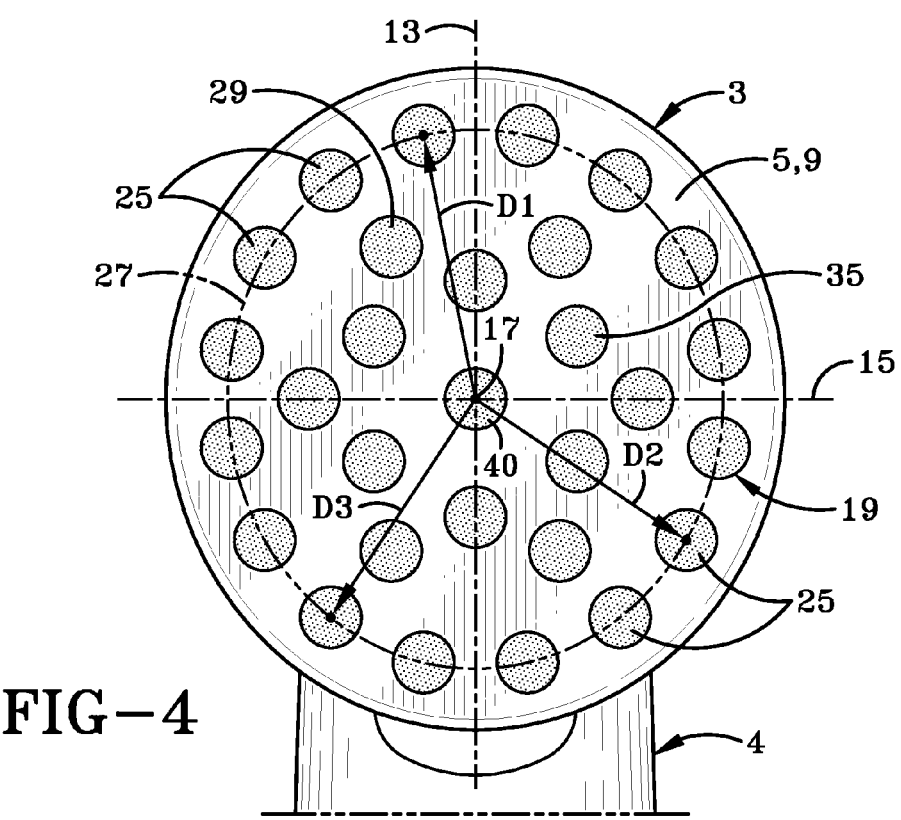
FIG. 4 is a view similar to FIG. 3 showing the outer series of bristle tufts forming a generally oval-shaped ring with three distance lines being shown thereon.

Outer series 19 (FIG. 4) has 16 equally circumferentially spaced bristle tufts, each of which is indicated as 25, which are the same as bristle tufts 11 shown in FIG. 2. Bristle tufts 25 are arranged on and form an imaginary outer ring indicated at 27 which preferably has a slightly oval shape as discussed above coinciding with major axis 13 and minor axis 15. This ring 27 of bristle tufts 25 is illustrated with three length or distance lines in FIG. 4, wherein line D1 will be slightly larger than line D2, and with line D3 having a distance inbetween that of D1 and D2. The remaining tufts 25 will be similarly spaced throughout ring 27. These three distance lines illustrate the preferable slight oval-shaped ring that is formed by the series of tufts 25. As shown in FIG. 4, none of the bristle tufts 25 lie on either of the major and minor axes 13 and 15.

Figure 5:
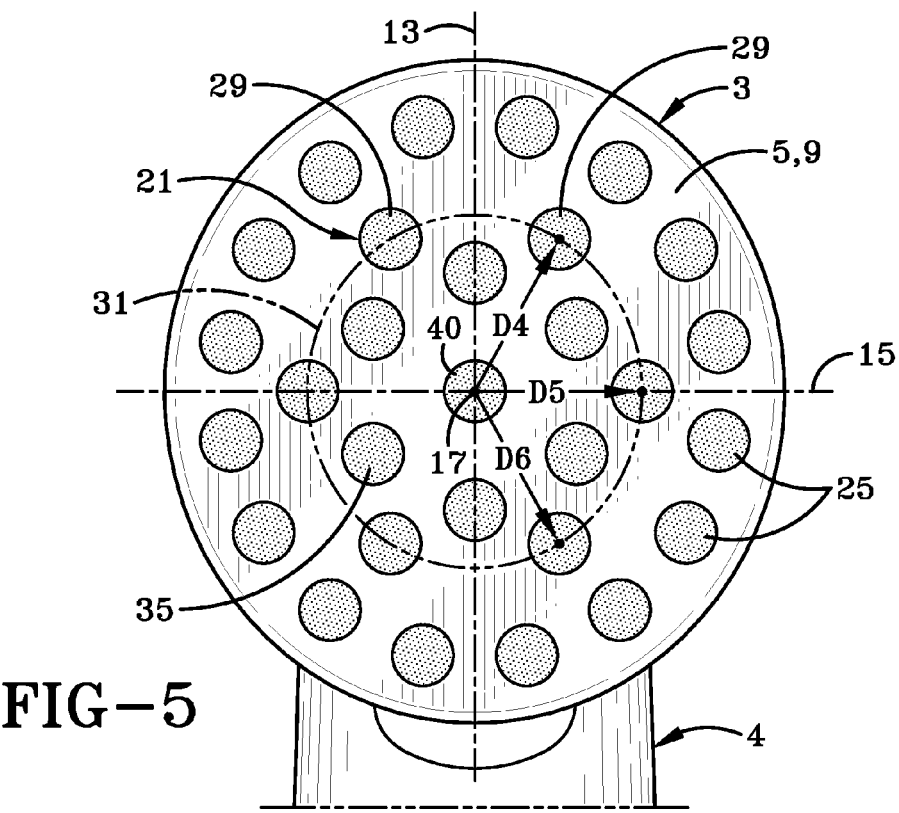
FIG. 5 is a view similar to FIG. 4 showing the intermediate series of bristle tufts forming a generally oval-shaped ring with three distance lines being shown thereon.

The details of the second or intermediate series of bristle tufts is shown in FIG. 5 and consists of six bristle tufts, each of which is indicated as 29, which again are similar to bristle tufts 11 and 25 discussed above. The six bristle tufts 29 are equally circumferentially spaced and arranged to form an imaginary intermediate ring 31 which preferably has a slightly oval shape lying concentrically within outer ring 27 and coinciding with major and minor axes 13 and 15. This slightly oval-shaped configuration of imaginary ring 31 formed by bristle tufts 29 is shown by a plurality of length or distance lines D4, D5 and D6. Distance line D4 will be slightly longer than distance line D5, and will be generally equal to distance line D6, again illustrating the slight oval shape of the imaginary ring 31 formed by the intermediate series 21 of six bristle tufts.

Furthermore, as shown in FIG. 5, the six bristle tufts 29 are equally circumferentially spaced with respect to each other with two of the bristle tufts lying on minor axis 15 and with none of the other four bristle tufts lying on any of the axes 13 or 15.

However, the bristle tufts forming outer ring 27 and intermediate ring 31 can have circular arrangements instead of slightly oval-shaped arrangements without affecting the concept of the present invention.

Figure 6:
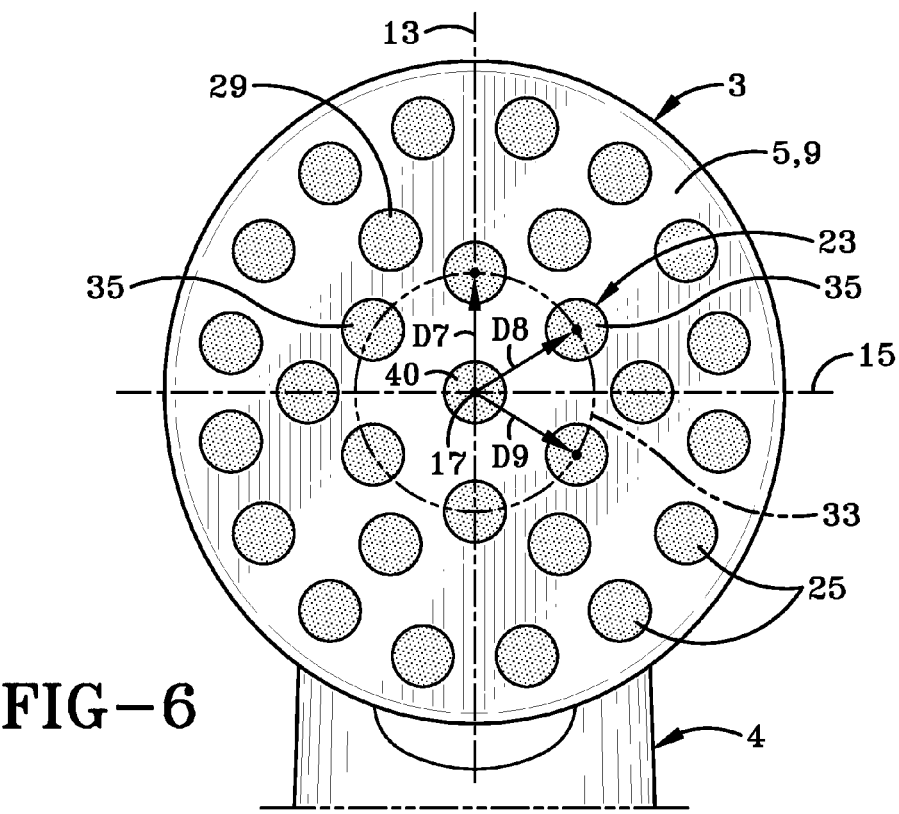
FIG. 6 is a view similar to FIGS. 4 and 5 showing the inner series of bristle tufts forming a circular-shaped ring with three distance lines being shown thereon.

The inner or third series 23 of bristle tufts lie on and form an imaginary circle indicated at 33, and consists of six equally circumferentially spaced bristle tufts 35, which again are similar to bristle tufts 11, 25 and 29 as discussed above. The six bristle tufts 35 which are arranged along imaginary circle 33 in contrast to the preferably slightly oval shape of imaginary rings 27 and 31. This is shown by distance lines D7, D8 and D9 which are equal in length. As shown in FIG. 6, the six bristle tufts of the inner series 23 which form imaginary circle 33, are concentric with respect to imaginary rings 27 and 31 and have the center point 17 as the center of the circle. Two of the bristle tufts 35 are located along the major axis 13 equally spaced on opposite sides of center point 17, with none of the remaining four tufts being located on either of the axes 13 or 15. Furthermore, FIG. 6 shows that each of the bristle tufts 35 of inner series 23 is located intermediate a pair of bristle tufts 29 of intermediate series 21.

Figure 7:
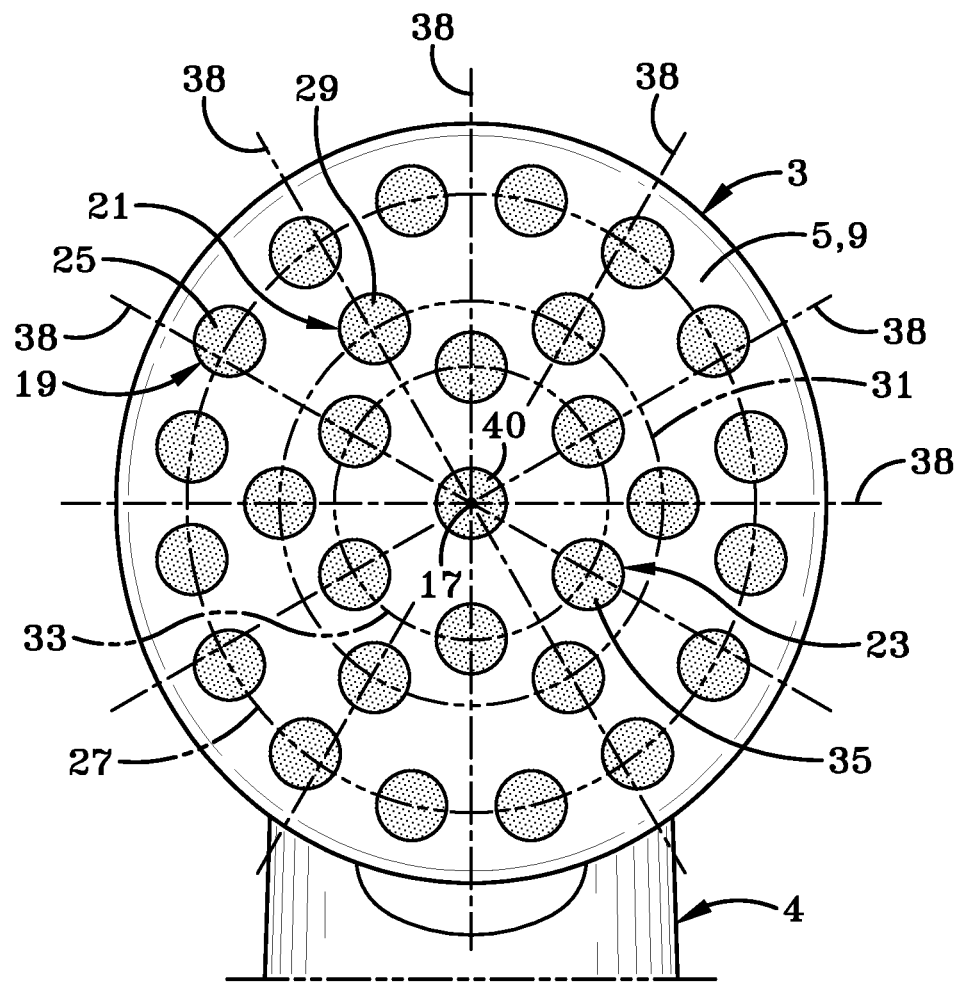
FIG. 7 is a view similar to FIGS. 3-6 showing a plurality of diameter lines extending through the three series of bristle tufts.

FIG. 7 shows another feature of the unique arrangement of bristle tufts. Twelve diameter lines 38 are used as examples, each of which is spaced 30 degrees with respect to the adjacent ones, extend through the center point 17. These diameter lines 38 or any other diameter line, will pass through no more than two of the bristle tufts of either the inner or intermediate series of bristle tufts. Thus, a diameter line will pass through only two of either the intermediate ring or inner ring of bristle tufts and may or may not pass through none or two of the bristle tufts of outer ring 27.

Thus, FIG. 7 shows the unique arrangement of the bristle tufts which are arranged in imaginary three rings formed by series of bristle tufts with the outer series 19 preferably having sixteen equally spaced tufts, none of which lie on either of the major or minor axes when arranged in a slightly oval shape, with the intermediate series 21 preferably consisting of six bristle tufts spaced equally circumferentially with respect to each other, and with the inner series 23 of bristle tufts 35 preferably having six bristle tufts and forming a generally circular configuration about center point 17, with each of the individual tufts 35 being located between outer pairs of bristle tufts 29 and with two of the bristle tufts 35 of the inner series lying on major axis 13. Preferably a single bristle tuft 40 is located at center point 17 as is the same construction as the bristle tufts 25, 29 and 35 of series 19, 21 and 23, respectively.

It is readily understood that support surface 9 could be circular with outer series 19 and intermediate series 21 being arranged in a circular or slightly oval configuration without appreciably affecting the concept of the present invention. The most important feature of the present invention is the unique arrangement of the bristle tufts in the three series of bristle tufts and their arrangement about center point 17 with or without center bristle tuft 40 and their arrangement with respect to any diameter passing through the center point of the support structure.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A brush head of a power-driven toothbrush comprising:
   a support structure;
   a plurality of bristle tufts attached to the support structure and extending upwardly therefrom, said plurality of bristle tufts including:
   a first series of bristle tufts forming an outer oval-shaped ring of bristle tufts having major and minor axes;
   wherein said first series of bristle tufts has only sixteen bristle tufts none of which lie on either of the major or minor axes of said oval-shaped outer ring;
   a second series of bristle tufts forming an intermediate ring of bristle tufts;
   a third series of bristle tufts forming an inner ring of bristle tufts;
   wherein said first, second and third series of bristle tufts are located generally concentrically with respect to each other and about a center point of the brush head;
   wherein the second and third series of bristle tufts have equal numbers of bristle tufts; and wherein each of the bristle tufts of the third series is intermediate a pair of bristle tufts of the second series;

and wherein a diameter line passing through the center point of the brush head passes through bristle tufts of only one of the second and third series of bristle tufts.

2. The brush head as defined in claim 1 wherein the intermediate ring of the second series of bristle is an oval-shaped ring concentric to the oval-shaped outer ring of the first series of bristle tufts.

3. The brush head as defined in claim 2 wherein the second series of bristle tufts include only six bristle tufts, two of which lie on the minor axis of the oval ring of the first series of tufts and none of the other four bristle tufts lie on the major axis of the oval ring of the first series of tufts.

4. The brush head as defined in claim 1 wherein all of the bristle tufts have the same length and diameter.

5. The brush head as defined in claim 1 including a center bristle tuft located on the center point of the brush head.

6. The brush head as defined in claim 5 wherein the center bristle tuft has the same length and diameter as the bristle tufts of the first, second and third series of bristle tufts.

7. The brush head as defined in claim 1 wherein the support structure is free of any bristle tufts located between the bristle tufts of the outer and intermediate ring of bristle tufts and between the bristle tufts of the intermediate and inner ring of bristle tufts.

8. A toothbrush comprising:
a handpiece;
a motor within the handpiece;
a brush head having a center point;
a plurality of bristle tufts mounted on and projecting upwardly from the brush head; said plurality of bristle tufts including:
a first series of bristle tufts located on an outer ring of bristle tufts;
a second series of bristle tufts located on an intermediate ring of bristle tufts;
a third series of bristle tufts located on an inner ring of bristle tufts;
said outer and intermediate rings of bristle tufts being generally oval-shaped with common major and minor axes, and wherein two of the bristle tufts of the inner ring lie on the major axis and two of the bristle tufts of the intermediate ring lie on the minor axis;
said first, second, and third series of bristle tufts located generally concentrically with respect to each other and about the center point of the brush head;
wherein a diameter line passing through a pair of diametrically aligned bristle tufts of the outer ring of bristle tufts will pass through a pair of bristle tufts of the inner ring of bristle tufts and is free of contact with a bristle tuft of the intermediate ring of bristle tufts.

9. The toothbrush as defined in claim 8 including a center bristle tuft located at the center point of the brush head.

10. The toothbrush as defined in claim 8 wherein the first series of bristle tufts includes only sixteen bristle tufts, the second series of bristle tufts includes only six bristle tufts, and the third series of bristle tufts includes only six bristle tufts.

11. The toothbrush as defined in claim 8 wherein none of the bristle tufts of the outer ring lie on either of the major and minor axes.

12. The toothbrush as defined in claim 8 wherein all of the bristle tufts are similar to each other having the same height and diameter.

13. A brush head of a power-driven toothbrush comprising:
a support structure;
a plurality of bristle tufts attached to the support structure and extending upwardly therefrom, said plurality of bristle tufts including:
a first series of bristle tufts forming an outer oval-shaped ring of bristle tufts having major and minor axes;
a second series of bristle tufts forming an intermediate ring of bristle tufts;
a third series of bristle tufts forming an inner ring of bristle tufts;
wherein said first, second and third series of bristle tufts are located generally concentrically with respect to each other and about a center point of the brush head;
wherein the second and third series of bristle tufts each includes only six bristle tufts; wherein each of the bristle tufts of the third series is intermediate a pair of bristle tufts of the second series; and wherein two of the bristle tufts of the third series of bristle tufts lie on the major axis and none of the remaining four bristle tufts lie on the minor axis;
and wherein a diameter line passing through the center point of the brush head passes through bristle tufts of only one of the second and third series of bristle tufts.

14. A toothbrush comprising:
a handpiece;
a motor within the handpiece;
a brush head having a center point;
a plurality of bristle tufts mounted on and projecting upwardly from the brush head; said plurality of bristle tufts including:
a first series of bristle tufts located on an outer ring of bristle tufts;
a second series of bristle tufts located on an intermediate ring of bristle tufts;
said outer and intermediate rings of bristle tufts being generally oval-shaped with common major and minor axes and wherein none of the bristle tufts of the outer ring lie on either of the major and minor axes;
a third series of bristle tufts located on an inner ring of bristle tufts;
said first, second, and third series of bristle tufts located generally concentrically with respect to each other and about the center point of the brush head; and
wherein a diameter line passing through a pair of diametrically aligned bristle tufts of the outer ring of bristle tufts will pass through a pair of bristle tufts of the inner ring of bristle tufts and is free of contact with a bristle tuft of the intermediate ring of bristle tufts.

15. The toothbrush as defined in claim 14 wherein two of the bristle tufts of the intermediate ring of bristle tufts lie on one of the axes of the brush head and none of the four remaining bristle tufts of the said intermediate ring of bristle tufts lie on either of the axes of said brush head.

16. The toothbrush as defined in claim 14 including a center bristle located on the center point of the brush head; and wherein the inner ring of bristle tufts has a circular configuration concentric about the center point of the brush head.

* * * * *